United States Patent [19]

Smigel et al.

[11] Patent Number: 4,925,655
[45] Date of Patent: May 15, 1990

[54] POWDER COMPOSITION FOR FORMING A MOUTHWASH

[75] Inventors: Irwin Smigel, New York, N.Y.; Said I. Raziq, St. Louis, Mo.

[73] Assignee: Robell Research

[21] Appl. No.: 164,248

[22] Filed: Mar. 4, 1988

[51] Int. Cl.$^5$ .......... A61K 7/18; A61K 7/20; A61K 7/26
[52] U.S. Cl. .................. 424/52; 424/53; 424/58
[58] Field of Search ................ 424/49–58, 424/53, 52

[56] References Cited

U.S. PATENT DOCUMENTS

| | | | |
|---|---|---|---|
| 2,035,267 | 3/1936 | Fleischman | 424/53 |
| 2,094,671 | 10/1937 | Poetschke | 424/53 |
| 3,518,343 | 6/1970 | Welsh et al. | 424/53 |
| 3,821,117 | 6/1974 | Breece et al. | 424/53 |
| 3,936,385 | 2/1976 | Cheng | 424/53 |

FOREIGN PATENT DOCUMENTS

| | | | |
|---|---|---|---|
| 118338 | 3/1944 | Australia | 424/53 |
| 354683 | 12/1937 | Italy | 424/53 |
| 60-116625A | 6/1985 | Japan | 424/53 |
| 424471907 | of 1907 | United Kingdom | 424/53 |

Primary Examiner—Shep K. Rose
Attorney, Agent, or Firm—Ladas & Parry

[57] ABSTRACT

A powder composition soluble in water to form a mouthwash having the following ingredients in percent by weight:

| Ingredient | Amount |
|---|---|
| Calcium peroxide | 0.5–80.0 |
| Sodium perborate | 0.5–80.0 |
| Sodium Bicarbonate | 1.0–95.0 |
| Tetrasodium pyrophosphate | 0.5–50.0 |
| Sodium lauryl sulfate | 0.5–4.0 |
| Sodium sacchrinate | 0.5–1.0 |
| Sorbisil TS-10 (hydrated silica) | 1.0–10.0 |
| Sodium benzoate | 0.5–10.0 |
| Citric acid (anhydrous) | 0.5–25.0 |
| Mint flavor | 0.5–1.0 |
| Potassium carbonate | 0.5–10.0 |
| Tea tree oil | 0.5–10.0 |
| Sodium monofluorophosphate | 0.1–1.0 |
| Thymol (5-methyl-2-isopropyl-1-phenol), hexyl resorcinol or mixtures thereof | .05–10.0 |

13 Claims, No Drawings

POWDER COMPOSITION FOR FORMING A MOUTHWASH

FIELD OF THE INVENTION

The invention relates to a powder composition which is soluble in water to form a mouthwash. The powder composition is particularly adapted for a mouthwash suitable not only for use with natural teeth but composite filling material as well.

BACKGROUND

In filling cavities from which dental caries have been removed, it has become an increasing practice to employ composite filling material which is similar in color to that of natural tooth material.

Such composite filling material is generally composed of a resinous substance which is polymerized in situ and which provides a hard bearing surface which has the natural appearance of a normal tooth.

Unfortunately, the composite filling material has inherent porosity and is relatively easily stained.

In a normal mouth, a salivary protein pellicle envelopes the tooth and is subject to plaque accumulation. Oral hygiene dictates the removal of the plaque accumulation in order to prevent decay of the tooth structure as well as serious diseases of the gums.

Disclosed in patents 4,405,599 and 4,603,045 are toothpaste compositions which are adapted for cleaning natural teeth and composite filling material as well.

SUMMARY OF THE INVENTION

An object of the invention is to provide a powder composition suitable for forming a mouthwash which is adapted for cleaning natural teeth as well as bonded composite filling material.

A particular object of the invention is to provide a powder composition suitable for forming a mouthwash which will reduce plaque accumulation on the teeth.

A further object of the invention is to provide a powder composition suitable for forming a mouthwash which will inhibit plaque growth in the pellicle on the teeth.

A further object of the invention is to provide a powder composition suitable for forming a mouthwash which will reduce the accumulation of stained pellicle on the teeth.

A further object of the invention is to provide a powder composition suitable for forming a mouthwash which will remove stained pellicle from the teeth.

In order to satisfy the above and further objects of the invention, there is provided a poqwder composition according to the invention containing a therapeutically effective amount of an active substance having the formula:

$$X_nOY_m$$

wherein

X is sodium, potassium, calcium, magnesium, zinc, aluminum or lithium, n is an integer equal to 1, 2 or 3, Y is a carbonate, sulfate, phosphate or oxygen, and m is an integer equal to 1, 2, or 3.

Preferably, the active substance is calcium peroxide.

In accordance with the invention, the active substance is present in the composition in an amount by weight of 0.5 to 80%.

In further accordance with the invention, an additional active substance is a germicide selected from the group consisting of thymol (5-methyl-2-isopropyl-1-phenol), hexyl resorcinol and mixtures thereof. The germicide can be present in the composition in an amount by weight of 0.05 to 10.0%.

In addition to the above substances, the powder composition contains suspending agents which prevent readherence of removed plaque from the teeth.

The powder composition may also contain a topical-fluoride supplying substance, such as sodium monofluorophosphate.

The powder composition may also contain a number of additional ingredients such as a detergent, for example, sodium lauryl sulfate, a sweetening agent such as sodium saccharinate, a gelling agent such as hydrated silica, a preservative such as sodium benzoate, an acid pH control agent such as citric acid, a flavoring material such as a mint flavoring, an alkaline pH control agent and tea tree oil as an antiseptic, germicide and gum healing substance.

In accordance with the above objects, a powder composition which will satisfy the objects of the invention, can be composed as follows, in per cent by weight:

| Ingredient | Amount |
| --- | --- |
| Calcium peroxide | 0.5–80.0 |
| Sodium perborate | 0.5–80.0 |
| Sodium bicarbonate | 1.0–95.0 |
| Tetrasodium pyrophosphate | 0.5–50.0 |
| Sodium lauryl sulfate | 0.5–4.0 |
| Sodium saccharinate | 0.5–1.0 |
| Sorbisil TS-10 (hydrated silica) | 1.0–10.03 |
| Sodium benzoate | 0.5–10.0 |
| Citric acid (anhydrous) | 0.5–25.0 |
| Mint flavor | 0.5–1.0 |
| Potassium carbonate | 0.5–10.0 |
| Tea tree oil | 0.5–10.0 |
| Sodium monofluorophosphate | 0.1–1.0 |
| Thymol (5-methyl-2-isopropyl-1-phenol), hexyl resorcinol and mixtures thereof | .05–10.0 |

The ingredients which have been incorporated into the powder composition are present in a carefully balanced amount to achieve the objects of the invention. The calcium peroxide is an active cleaning ingredient which removes stained pellicle and reduces accumulation of plaque and stained pellicle.

The thymol and hexyl resorcinol are alkylated hydroxy and dihydroxy benzene compounds which are active germicides. The compounds can be used individually or in admixture.

The sodium perborate, sodium bicarbonate, tetrasodium pyrophosphate and potassium carbonate are oxidizing agents having cleansing properties and also serving as suspension agents to prevent readherence of removed material on the teeth. The sodium bicarbonate and potassium carbonate are also alkalizers and additionally the potassium carbonate serves as a chelating agent to keep the removed material in suspension. The sodium perborate can be combined with or replaced by sodium percarbonate.

The invention covers the above ingredients as well as their obvious equivalents.

The sodium lauryl sulfate is a detergent.

The sodium saccharinate is a sweetening agent serving as a flavoring material, and the amount thereof can be varied according to the desired taste characteristic to be provided for the composition.

The hydrated silica is a gelling agent.

The sodium benzoate is a preservative.

The citric acid is a pH acid control agent.

The mint flavor and its amount are functions of the desired taste to be given to the powder composition and the flavor can be methanol, spearmint or the like. The tea tree oil is an antiseptic and gum healing agent.

The sodium monofluorophosphate is an active agent which is compatible in the overall composition and provides topical fluoride for inhibiting tooth decay.

DETAILED DESCRIPTION OF A PREFERRED EMBODIMENT

One of the most important advances in dentistry in the past twenty-five years has been the development of the composite (tooth colored) restoration. This has revolutionized the profession from an esthetic concept. This, coupled with the evolution of light activation with its capability of controlling setting time and the dentist's ability to etch the enamel of teeth and thus bond the composite material directly onto the tooth, is known as bonding. Bonding enables the dentist to close spaces between teeth, repair chips in teeth, cover discolorations and reshape abnormally shaped teeth. This coupled with the imminent development of composites for chewing surfaces of posterior teeth is expected to make the composite filling material the overwhelming material of choice in dentistry. However, the composite material for all of its advantages is inherently porous and is subject to staining. There are two types of composite filling material:

A. The conventional material which is composed of 76% inorganic filler material, such as quartz or Barium glass and 24% Resin Matrix, such as BIS GMA which is the reactive product of BIS Phenol A and Glycidyl Methyl acrylic.

B. Microfill-composed of 35–55% inorganic filler such as fused silica and 45–65% Resin Matrix, generally BIS GMA.

The present invention provides a powder composition which is soluble in water to form a mouthwash capable of cleaning natural teeth as well as the composite filling material, and inhibiting plaque build-up thereon. The composition consists essentially of the following ingredients given in percent by weight.

| Ingredient | Amount |
| --- | --- |
| Calcium peroxide | 5.00 |
| Sodium perborate | 5.00 |
| Sodium bicarbonate | 51.50 |
| Tetrasodium pyrophosphate | 7.00 |
| Sodium lauryl sulfate | 1.50 |
| Sodium saccharinate | 0.50 |
| Sorbisil TS-10 (hydrated silica) | 2.50 |
| Sodium benzoate | 1.50 |
| Citric acid (anhydrous) | 11.50 |
| Mint flavor | 1.00 |
| Potassium carbonate | 8.00 |
| Tea tree oil | 4.00 |
| Sodium mono fluorophosphate | 1.00 |
| Thymol (5-methyl-2-isopropyl-1-phenol) | .25 |

The above composition is soluble in water to form a mouthwash which was found to be exceptionally effective in its ability to retard plaque growth, reduce stained pellicle accumulation from various staining agents such as coffee, tea and various salts, and to remove stained pellicle both from normal teeth as well as composite filling material.

In order to produce the powder composition, the ingredients are combined in a mixer and thoroughly mixed and thereafter pulverized to a mesh size of between 10 and 30. The resulting powder composition is soluble in water and is effective as a mouthwash to achieve the objectives as given above. The powder composition has been found effective when dissolved in water in a concentration of 1 part powder composition to 1 to 10 parts water. Preferably, the powder composition is dissolved in water in a ratio of 1 part powder composition to 4 parts water.

While the invention has been described in connection with specific embodiments thereof, it will become apparent to those skilled in the art that various equivalents may be used within the scope and spirit of the invention as defined by the attached claims.

What is claimed is:

1. A powder composition which is added to water to form a mouthwash comprising the following ingredients in percent by weight:

| Ingredient | Amount |
| --- | --- |
| Calcium peroxide | 0.5–80.0 |
| Sodium perborate | 0.5–80.0 |
| Sodium bicarbonate | 1.0–95.0 |
| Tetrasodium pyrophosphate | 0.5–50.0 |
| Sodium lauryl sulfate | 0.5–4.0 |
| a sweetener | 0.5–1.0 |
| a gelling agent | 1.0–10.0 |
| an acid pH control agent | 0.5–25.0 |
| Potassium carbonate | 0.5–10.0 |
| Tea tree oil | 0.5–10.0 |
| Thymol, hexyl resorcinol and mixtures thereof | .05–10.0 |

2. A powder composition as claimed in claim 1 further comprising a topical fluoride supplying substance.

3. A powder composition as claimed in claim 2 wherein said topical fluoride supplying substance is sodium monofluorophosphate.

4. A powder composition as claimed in claim 1 which has been pulverized to a mesh size of 10 to 30.

5. A powder composition as claimed in claim 1 further comprising a germicide consisting essentially of alkylated hydroxy and dihydroxy benzene in an amount of 0.05–10% by weight.

6. A powder composition as claimed in claim 5 wherein said germicide is selected from the group consisting of thymol, hexyl resorcinol and mixtures thereof.

7. A method of removing from the teeth plaqu accumulation and stained pellicle and inhibiting plaque growth and accumulation of stained pellicle comprising rinsing the mouth of a user with a mouthwash produced by adding a powder composition to water, said powder composition consisting essentially of the following ingredients in percent by weight:

| Ingredient | Amount |
| --- | --- |
| Calcium peroxide | 0.5–80.0 |
| Sodium perborate | 0.5–80.0 |
| Sodium bicarbonate | 1.0–95.0 |
| Tetrasodium pyrophosphate | 0.5–50.0 |
| Sodium lauryl sulfate | 0.5–4.0 |
| a sweetener | 0.5–1.0 |
| a gelling agent | 1.0–10.0 |
| an acid pH control agent | 0.5–25.0 |
| Potassium carbonate | 0.5–10.0 |
| Tea tree oil | 0.5–10.0 |
| Thymol, hexyl resorcinol and mixtures thereof | .05–10.0 |

8. A method as claimed in claim 7 wherein said composition further comprises a germicide consisting essentially of alkylated hydroxy and dihydroxy benzene in an amount of 0.05-10% by weight.

9. A method as claimed in claim 8 wherein said germacide is selected from the group consisting of thymol, hexyl resorcinol and mixtures thereof.

10. A method as claimed in claim 9 wherein said ingredient is present in an amount by weight of 0.5 to 80.0% and the germicide in an amount by weight of 0.05 to 10.0%.

11. A method as claimed in claim 7 further comprising a topical fluoride supplying substance.

12. A method as claimed in claim 7 in which the composition has been pulverized to a mesh size of 10 to 30.

13. A method as claimed in claim 7 wherein the composition further comprises a germicide selected from the group consisting of thymol, hexyl resorcinol and mixtures thereof in an amount by weight of 0.05 to 10.0%.

* * * * *